United States Patent [19]

Nelson

[11] 4,208,409

[45] Jun. 17, 1980

[54] N-[(PHOSPHINYL OR PHOSPHINOTHIOYL)AMINO]THIO-METHYLCARBAMATES AND PESTICIDAL METHODS

[75] Inventor: Stephen J. Nelson, Comstock Township, Kalamazoo County, Mich.

[73] Assignee: The Upjohn Company, Kalamazoo, Mich.

[21] Appl. No.: 962,266

[22] Filed: Nov. 20, 1978

Related U.S. Application Data

[63] Continuation-in-part of Ser. No. 874,959, Feb. 3, 1978, abandoned, which is a continuation-in-part of Ser. No. 765,807, Feb. 4, 1977, Pat. No. 4,081,536.

[51] Int. Cl.$^2$ .......................... A01N 9/36; C07F 9/24
[52] U.S. Cl. .................................... 424/209; 260/937; 260/346.73; 424/202; 424/203; 549/5; 549/7
[58] Field of Search .............. 260/937, 327 M, 346.73; 424/209, 202, 203

[56] References Cited

U.S. PATENT DOCUMENTS

| | | | |
|---|---|---|---|
| 3,932,403 | 1/1976 | Ashton et al. | 260/937 |
| 4,024,237 | 5/1977 | Engel | 260/346.22 |

*Primary Examiner*—Anton H. Sutto
*Attorney, Agent, or Firm*—Sidney B. Williams, Jr.

[57] ABSTRACT

Some new phosphinic acid derivatives of aminothio methylcarbamates have been synthesized and tested as pesticides. The new compounds are active against insects, mites, and nematodes. The N-[(phosphinyl)amino]thio- and N-[(phosphinothioyl)amino]thio- methylcarbamates are readily prepared by the general procedure of reacting a phosphinic acid amide with sulfur dichloride so as to obtain the corresponding N-(chlorothio)phosphinic acid amide which reactant will react with a methylcarbamate so as to produce the corresponding object compounds, the N-[(phosphinothioyl)amino]thio- methylcarbamates of this invention. Various formulations for pesticidal use are described along with appropriate rates of application.

57 Claims, No Drawings

N-[(PHOSPHINYL OR PHOSPHINOTHIOYL)AMINO]THIO-METHYL-CARBAMATES AND PESTICIDAL METHODS

CROSS-REFERENCES TO RELATED APPLICATIONS

This application is a continuation-in-part of application Ser. No. 874,959, filed Feb. 3, 1978, now abandoned, which is a continuation-in-part of application Ser. No. 765,807, filed Feb. 4, 1977 and now U.S. Pat. No. 4,081,536.

SUMMARY OF THE INVENTION

This invention pertains to some new organic compounds, to a process for preparing them, and to formulations of them suitable for pesticidal use. The invention is more particularly directed to phosphinic acid derivatives of aminothio methylcarbamates.

Substituted-thio derivatives of methylcarbamate pesticides are known and U.S. Pat. Nos. 3,781,331, issued Dec. 25, 1973, and No. 3,794,733, issued Feb. 26, 1974, can be referred to for relevant status of the art. The first patent being relevant to acylaminothio derivatives of methyl carbamate pesticides. Belgium Pat. No. 860,844 issued May 15, 1978, discloses N-[(phosphinyl)amino]thio-methylcarbamates. However, insofar as is presently known, no one has prepared phosphinic acid derivatives of aminothio methylcarbamate pesticides from cyclic phosphoramidothioates.

Some of the objectives of this invention include the obtainment of methylcarbamate pesticides having an effectiveness equal to or greater than that of the parent compounds against pests, such methyl carbamate pesticides having reduced mammalian toxicity, reduced phytotoxicity, and longer residual action. These objectives have been realized with the new compounds of this invention. Other worthwhile objectives will be recognized by those skilled in the art.

DETAILED DESCRIPTION OF THE INVENTION

The indicated N-[(phosphinyl)amino]thio- and N-[(phosphinothioy)amino]thio- methylcarbamate pesticides of this invention are represented by the following schematic formula:

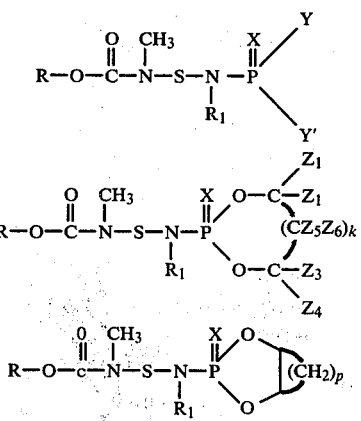

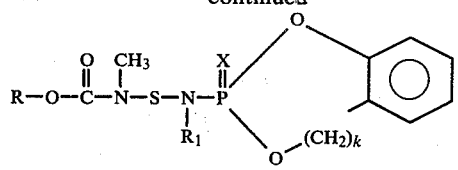

wherein, R is selected from the group consisting of

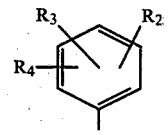

wherein $R_2$, $R_3$, and $R_4$ are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and $—N=CHN(CH_3)_2$;

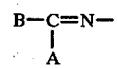

wherein A and B are the same or different and are selected from the group consisting of lower-alkyl of one to five carbon atoms, inclusive, lower-alkylthio of one to five carbon atoms, inclusive, monocyano substituted alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, cyano, alkoxy having one to five carbon atoms, inclusive, phenyl, and hydrogen, with the proviso that when B is hydrogen, A is of the formula

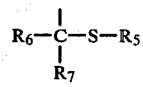

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula

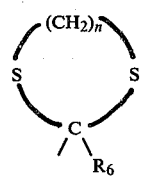

wherein n is 2 or 3 and the alkylene portion of the ring is unsubstituted or substituted with one or two methyl groups; A and B taken together with the carbon atom to which they are attached form a dithio heterocyclic of the formula

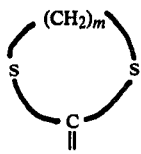

wherein m is 2 or 3 and the alkylene portion of the ring is unsubstituted or substituted with one to two methyl groups; and c.

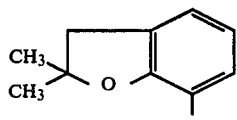

$R_1$ is selected from the group consisting of loweralkyl, phenyl, substituted phenyl, phenyl loweralkyl, and cycloalkyl; X is oxygen or sulfur; and Y and Y' are the same or different and are selected from the group consisting of lower-alkyl, lower-alkoxy, lower-alkylthio, cycloalkyl, phenyl, substituted phenyl, phenoxy, substituted phenoxy, thiophenoxy, and substituted thiophenoxy; $Z_1$ through $Z_8$ are the same or different and are selected from the group consisting of hydrogen, methyl and ethyl; k is zero or one, p is three or four and Ra is selected from the group consisting of hydrogen, lower alkyl, lower alkoxy and halogen.

In the foregoing designation of variables, "lower-alkoxy" means methoxy, ethoxy, propoxy, isopropoxy, butoxy, pentoxy, and the further isomeric forms thereof. Likewise, "lower-alkylthio" means methylthio, ethylthio, propylthio, isopropylthio, butylthio, pentylthio, and further isomeric forms thereof.

"Lower-alkyl" means methyl, ethyl, propyl, butyl, pentyl, and the isomeric forms thereof; while "cycloalkyl" means cyclopropyl, cyclobutyl, cyclopentyl, and cyclohexyl optionally substituted with methyl, ethyl, and propyl to a total of nine carbon atoms.

"Phenlower-alkyl" means benzyl, phenethyl, phenpropyl, phenbutyl, phenpentyl, and isomeric forms thereof.

"Substituted-phenyl" means lower-alkyl-, loweralkoxy-, halogen-, nitro-, and cyano-substitutedphenyl. There can be combinations of substituents such as 4-propyl-2-methyl-, 2-chloro-4-methyl, 3,4-diethoxy, 3-cyano-4-ethoxy-phenyl, and the like. Practically speaking, the "substituted-phenyl" group is limited to a total of ten carbon atoms, e.g., 4-isobutylphenyl.

"Substituted phenoxy" means lower-alkyl, loweralkoxy, halogen, nitro, and cyano substituted phenoxy. There can be combinations of substituents such as 4-propyl-2-methyl-, 2-chloro-4-methyl-, 3,4-diethoxy, 3-cyano-4-ethoxy-phenoxy and the like. The substituted phenoxy is limited to a total of ten carbon atoms, e.g., 4-isobutylphenoxy.

"Substituted thiophenoxy" means lower-alkyl, lower-alkoxy, halogen, nitro, and cyano substituted thiophenoxy. There can be combinations of substituents such as 4-propyl-2-methyl-, 2-chloro-4-methyl-, 3,4-diethoxy, and the like. The substituted thiophenoxy is limited to a total of ten carbon atoms, e.g., 4-isobutylthiophenoxy and the like.

The new N-[(phosphinyl)amino]thio- and N-[(phosphinothioyl)amino]thio- methylcarbamate pesticidal compounds of this invention according to Formula I are prepared in accordance with the process of the invention by reacting a selected methylcarbamate precursor with an N-(halothio)phosphinic acid amide. A schematic representation of the reaction, preparing compounds of Formula I as an example, is as follows:

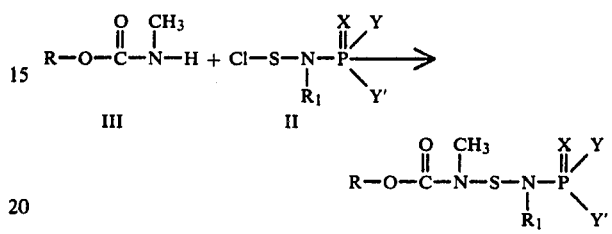

wherein R, $R_1$, X, Y, and Y' are the same as above.

The reaction is effected in the cold, preferably −20° to 25° C., in the presence of a suitable acid acceptor and an inert organic medium. Illustrative of suitable acid acceptors are trialkyl amine, (e.g., triethylamine), pyridine and lutidine. Illustrative of the organic media for the reaction are dimethylformamide, diethylether, hexane, tetrahydrofuran, and acetonitrile. When non-polar solvents and some polar solvents are used, cuprous chloride and aluminum chloride may be used to catalyse the reaction.

The desired compounds according to Formula I, I', I" and I'" are recovered and purified according to conventional methods. Filtration, solvent evaporation, chromatography, crystallization, and combinations thereof are employed. Some of the compounds are obtained as crystals while others are purified as oils. The phosphinic acid N-chlorothioamides of Formula II can be prepared by reacting the corresponding phosphinic acid amides with sulfur dichloride at about −20° to 25° C. in the presence of a suitable acid acceptor and an inert inorganic media. The phosphinic acid amides are either readily available or can be prepared by methods described in the prior art; for example, in Methoden der Organishen Chemie (Houben-Weyl) Vol. 12, part 2, page 413; and Vol. 12, part 1, pages 529 and 595, Georg Thieme Verlag (Pub.), Stuutgart, Germany, 1963.

The preferred compounds of this invention are those having the formulae

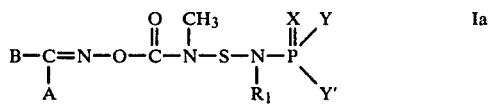
Ia

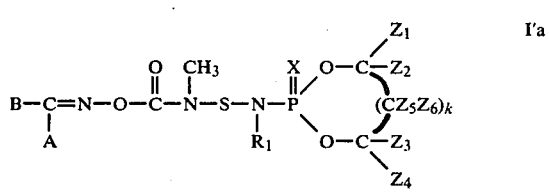
I'a

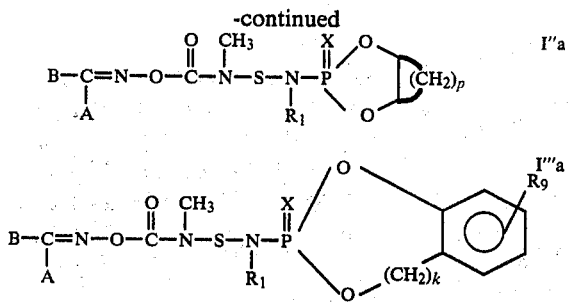

wherein A and B are the same or different and are selected from the group consisting of lower-alkyl of one to five carbon atoms, inclusive, lower-alkyl-thio of one to five carbon atoms, inclusive, mono-cyano substituted alkylthio of one to five carbon atoms, inclusive, phenylthio wherein phenyl is unsubstituted or substituted with one to three substituents, same or different, selected from the group consisting of halogen and lower alkyl of one to four carbon atoms, inclusive, cyano, alkoxy having one to five carbon atoms, inclusive, phenyl, and $R_1$, X, Y, Y', $Z_1$ through $Z_6$, Ra, K and p are the same as above.

Some of the compounds of Formula Ia where Y and Y' for the radical

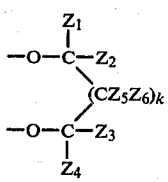

wherein $Z_1$ through $Z_6$ and k are the same as above, exhibit an unexpected crystallinity. For example, the compound N-[[[[[(5,5-dimethyl-2-thioxo-1,3,2-dioxaphosphorinan-2-yl)t-butylamino]thio]methylamino]carbonyl]oxy]ethanimidothioate is extremely crystalline. The physical properties associated with the crystallinity facilitate isolation of the product from the reaction mixture. Further, the highly crystalline compounds allow for wettable powder formulation which have advantageous properties such as reduced compaction, flowability and high concentrations of active ingredients.

The following described preparations of new compounds according to Formula I are indicative of the scope of this invention and are not to be construed as limitative. Those skilled in the art will promptly recognize appropriate variations from the procedure both as to methylcarbamate precursors as well as reaction conditions and techniques. These examples indicate the best mode presently known to the inventor.

PREPARATION I

Reactant O,O-Diethyl N-(Chlorothio)-N-(n-propyl)-Phosphoramidothioate

A solution of 2.98 gm. (0.014 mole) O,O-diethyl n-propylphosphoramidothioate in 10 ml. hexane and 2 ml. triethylamine is added to a cold (0° C.) solution of 1.0 ml. (0.016 mole) sulfur dichloride in 10 ml. hexane slowly and with stirring. There is vigorous reaction and heavy precipitation of triethylamine hydrochloride. An additional 20 ml. hexane is added. The reaction mixture is kept at 0° to 5° C. and stirred for 30 minutes, then it is filtered. The filtrate is concentrated to a pale yellow oil by evaporating the hexane under reduced pressure. The oil comprises the desired O,O-diethyl N-(chlorothio)-n-propylphosphoramidothioate which can be used for further reactions with N-methylcarbamates.

PREPARATION II

Reactant O,O-Diethyl N-(chlorothio)-N-isopropylphosphoramidothioate

A solution consisting of 9.95 gm. (0.0471 mole) of O,O-diethylisopropylphosphoramidothioate and 6.5 ml triethylamine is added slowly and with stirring to a cooled solution consisting of 3.0 ml (0.047 mole) of sulfur dichloride and 150 ml hexane. The temperature is maintained at 0° to 5° C. during the addition and for 30 minutes while stirring is continued. The reaction mixture is filtered and the precipitated salts that are collected on the filter are washed with hexane. The filtrate and hexane washings are combined and the hexane is removed by evaporation under reduced pressure. There is thus obtained the desired reactant O,O-diethylisopropylphosphoramidothioate as an orange-colored oil.

EXAMPLE 1

Preparation of the compound 4-(dimethylamino)-3,5-xylyl [[(diethoxyphosphinothioyl)-n-propylamino]thio]methylcarbamate The crude O,O-diethyl N-(chlorothio)-n-propylphosphoramidothioate (prepared in Preparation I) is cooled in an ice-bath and 2.79 gm. (0.013 mole) of 4-(dimethylamino)-3,5-xylyl methylcarbamate dissolved in 20 ml dimethylformamide (with 2 ml triethylamine added) are mixed as a batch. This reaction mixture is stirred at 25° C. for four hours, and then diluted with hexane. The organic solution is washed with water, dried over anhydrous sodium sulfate, and the organic solvents are removed by evaporation under reduced pressure. The residue thus obtained is transferred to a column of "Florisil". The chromatogram is developed first with a solvent mixture consisting of 10 percent diethyl ether in petroleum ether, and finally with 30 percent diethyl ether in petroleum ether. After collecting the later eluate and removing the solvents by evaporation under reduced pressure, there is obtained the desired 4-(dimethylamino)-3,5-xylyl [[(diethoxyphosphinothioyl)-n-propylamino]thio]methylcarbamate as a yellow oil.

Analysis:

Calc'd for $C_{19}H_{34}N_3O_4PS_2$: C, 49.22; H, 7.39; N, 9.06. Found: C, 49.84; H, 7.89; N, 8.52.

EXAMPLE 2

Preparation of the compound 2-isopropoxyphenyl [[(diethoxyphosphinothioyl) anilino]thio]methylcarbamate Part A Preparation of reactant O,O-Diethyl N-(chlorothio)phenylphosphoramidothioate A solution consisting of 6.69 gm (0.0314 mole of O,O-diethylphenylphosphoramidothioate, 25 ml ether, and 4.4 ml (0.032 mole) triethylamine is added dropwise with stirring, during an interval of 30 minutes to a chilled (−10° C.) solution consisting of 2.0 ml (0.031 mole) sulfur dichloride and 25 ml diethyl ether. Stirring is continued for 30 minutes in the cold. The precipitate that is formed is collected on a filter and the filter cake is washed with diethyl ether. After combining the original filtrate with the ether wash, the ether is removed by evaporation under reduced pressure to give the desired O,O-diethyl N-(chlorothio)phenylphosphoramidothioate as a yellow oil.

Part B 2-Isopropoxyphenyl [[(diethoxyphosphinothioyl)anilino]thio]methylcarbamate The O,O-diethyl N-(chlorothio)phenylphosphoramidothioate as a yellow oil obtained in Part A, above, is dissolved in a minimal amount of diethyl ether (about 5 ml) and the ether solution is added to a cooled (0° C.) solution consisting of 6.34 gm (0.030 mole) of 2-isopropoxyphenyl methylcarbamate and 20 ml dimethylformamide. This reaction mixture is stirred as it is permitted to warm to 25° C., and stirring is continued for four hours. The mixture is then diluted with 100 ml water and extracted with diethyl ether. The ether phase is recovered, washed with water, and dried over anhydrous sodium sulfate. The ether is removed by evaporation under reduced pressure. The oily residue thus obtained is chromatographed through a column of silica gel. Development is with methylene chloride. After removing the methylene chloride by evaporation under reduced pressure, there is obtained 1.02 gm. of the crude product as an amber oil which is crystallized from petroleum ether having a boiling range between 30° and 60° C. to give 2-isopropoxyphenyl [[(diethoxyphosphinothioyl)anilino]thio]methylcarbamate as colorless crystals having a melting point at 69° to 70.5° C.

Analysis: Calc'd for $C_{21}H_{29}N_2O_5PS_2$: C, 52.04; H, 6.03; N, 5.78. Found; C, 52.03; H, 6.18; N, 5.78.

EXAMPLE 3

Preparation of 2-Isopropoxyphenyl [[(diethoxyphosphinothioyl)-n-propylamino]thio]methylcarbamate Following the same procedure as described in Example 2, Part B, but substituting O,O-diethyl N-(chlorothio)-n-propylphosphoramidothioate (prepared as in Preparation I) for the O,O-diethyl N-(chlorothio)phenylphosphoramidothioate, there is prepared the corresponding 2-isopropoxyphenyl [[(diethoxyphosphinothioyl)propylamino]thio]methylcarbamate as an amber oil.

Analysis: Calc'd for $C_{18}H_{31}N_2O_5PS_2$: C, 47.98; H, 6.94; N, 6.22. Found: C, 47.47; H, 6.90; N, 6.26.

EXAMPLE 4

Preparation of the compound 3-isopropylphenyl [[(diethoxyphosphinothioyl)-isopropylamino]thio]methylcarbamate Following the procedure as described in Example 2, Parts A and B, but appropriately substituting O,O-diethyl isopropylphosphoramidothioate for O,O-diethyl phenylphosphoramidothioate and substituting 3-isopropylphenyl methylcarbamate for 2-isopropoxyphenyl methylcarbamate, there is prepared 3-isopropylphenyl [[(diethoxyphosphinothioyl)isopropylamino]thio]methylcarbamate as an amber oil.

Analysis: Calc'd for $C_{18}H_{31}N_2O_4PS_2$: C, 49.75; H, 7.19; N, 6.45. Found; C, 49.43; H, 7.09; N, 6.39.

EXAMPLE 5

Preparation of Methyl N-[[[[[(dimethoxyphosphinothioyl)methylamino]thio]methylamino]carbonyl]oxy]ethanimidothioate Starting with the known compound methyl N-[[(methylamino)carbonyl]oxy]ethanimidothioate, and the appropriate phosphoramidothioate, the following new N-[(phosphinyl)amino]thio carbamates and N-[(phosphinothioyl)amino]thio carbamates are prepared by procedures similar to Example 2, Part B.

Methyl N-[[[[[(dimethoxyphosphinothioyl)methylamino]thio]methylamino]carbonyl]oxy]ethanimidothioate, m.p. 57° to 58° C.

Analysis: Calc'd for $C_8H_{18}N_3S_3O_4P$: C, 27.66; H, 5.22; N, 12.10. Found; C, 27.88; H, 5.27; N, 11.95.

Methyl N-[[[[[(dimethoxyphosphinothioyl)isopropylamino]thio]methylamino]carbonyl]oxy]ethanimidothioate, m.p. 88° to 89° C.

Analysis: Calc'd for $C_{10}H_{22}N_3O_4PS_3$: C, 31.99; H, 5.91; N, 11.19. Found; C, 31.99; H, 5.86; N, 10.93.

Methyl N-[[[[[(dimethoxyphosphinothioyl)n-butylamino]thio]methylamino]carbonyl]oxy]ethanimidothioate, m.p. 60° to 61° C.

Analysis: Calc'd for $C_{11}H_{24}N_3O_4PS_3$: C, 33.92; H, 6.21; N, 10.79. Found; C, 33.84; H, 6.26; N, 10.44.

Methyl N-[[[[[(diethoxyphosphinothioyl)methylamino]thio]methylamino]carbonyl]oxy]ethanimidothioate.

Analysis: Calc'd for $C_{10}H_{22}N_3O_4PS_3$: C, 31.99; H, 5.91; N, 11.19. Found; C, 32.00; H, 5.96; N, 10.58.

Methyl N-[[[[[(diethoxyphosphinothioyl)isopropylamino]thio]methylamino]carbonyl]oxy]ethanimidothioate, m.p. 72° to 73° C.

Analysis: Calc'd for $C_{12}H_{26}N_3O_4PS_3$: C, 35.71; H, 6.50; N, 10.41. Found; C, 35.77; H, 6.74; N, 10.09.

Methyl N-[[[[[(diethoxyphosphinothioyl)-n-propylamino]thio]methylamino]carbonyl]oxy]ethanimidothioate.

Analysis: Calc'd for $C_{12}H_{26}N_3PS_3$: C, 35.71; H, 6.50; N, 10.41. Found; C, 35.48; H, 6.46; N, 9.82.

Methyl N-[[[[[(diethoxyphosphinothioyl)anilino]thio]methylamino]carbonyl]oxy]ethanimidothioate, m.p. 68° to 69° C.

Analysis: Calc'd for $C_{15}H_{24}N_3O_4PS_3$: C, 41.17; H, 5.53; N, 9.60. Found; C, 40.80; H, 5.43; N, 9.37.

Methyl N-[[[[[(diethoxyphosphinyl)methylamino]thio]methylamino]carbonyl]oxy]ethanimidothioate.

Analysis: Calc'd for $C_{10}H_{22}N_3O_5PS_2$: C, 33.42; H, 6.17; N, 11.69. Found; C, 33.26; H, 6.17; N, 11.28.

Methyl N-[[[[[[methoxy(methylthio)phosphinyl]methylamino]thio]methylamino]carbonyl]oxy]ethanimidothioate, as an amber oil.

Analysis: Calc'd for $C_8H_{18}N_3O_4PS_3$: C, 27.66; H, 5.22; N, 12.09. Found; C, 27.44; H, 5.50; N, 11.60.

Methyl N-[[[[[[methoxy(phenyl)phosphinothioyl]isopropylamino]thio]methylamino]carbonyl]oxy]ethanimidothioate, m.p. 103° to 105° C.

Analysis: Calc'd for $C_{15}H_{24}N_3O_4PS_2$: C, 42.74; H, 5.74; N, 9.97. Found; C, 42.62; H, 5.67; N, 10.02.

Methyl N-[[[[[[methoxy(phenyl)phosphinothioyl]methylamino]thio]methylamino]carbonyl]oxy]ethanimidothioate, m.p. 109° to 110° C.

Analysis: Calc'd for $C_{13}H_{20}N_3S_3O_3P$: C, 39.68; H, 5.12; N, 10.68. Found; C, 39.73; H, 5.32; N, 10.92.

Methyl N-[[[[[[methoxy(methyl)phosphinothioyl]methylamino]thio]methylamino]carbonyl]pxy]ethanimidothioate, m.p. 87° to 88° C.

Analysis: Calc'd for $C_8H_{18}N_3O_3S_3P$: C, 28.99; H, 5.47; N, 12.68. Found; C, 29.61; H, 6.00; N, 12.84.

Methyl N-[[[[[isopropoxy(phenyl)phosphinothioyl]isopropylamino]thio]methylamino]carbonyl]oxy]ethanimidothioate, m.p. 100° to 102° C.

Analysis: Calc'd for $C_{17}H_{28}N_3O_3S_3P$: C, 45.42; H, 6.28; N, 9.34. Found; C, 45.00; H, 6.54; N, 9.32.

Methyl N-[[[[[methyl(phenoxy)phosphinothioyl]methylamino]thio]methylamino]carbonyl]oxy]ethanimidothioate, m.p. 65° to 67° C.

Analysis: Calc'd for $C_{13}H_{20}N_3O_3PS_3$: C, 39.68; H, 5.12; N, 10.68. Found; C, 39.74; H, 5.30; N, 10.79.

Methyl N-[[[[[isopropoxy(methyl)phosphinothioyl]isopropylamino]thio]methylamino]carbonyl]oxy]ethanimidothioate, m.p. 90° to 92° C.

Analysis: Calc'd for $C_{12}H_{26}N_3O_3PS_3$: C, 37.19; H, 6.76; N, 10.84. Found; C, 37.39; H, 7.06; N, 10.72.

Methyl N-[[[[[methoxy(methyl)phosphinothioyl]isopropylamino]thio]methylamino]carbonyl]oxy]ethanimidothioate, m.p. 91° to 93° C.

Analysis: Calc'd for $C_{10}H_{22}N_3O_3PS_3$: C, 33.41; H, 6.17; N, 11.69. Found; C, 33.42; H, 6.43; N, 11.90.

Methyl N-[[[[[methyl(phenoxy)phosphinothioyl]isopropylamino]thio]methylamino]carbonyl]oxy]ethanimidothioate, m.p. 70° to 72° C.

Analysis: Calc'd for $C_{15}H_{24}N_3O_3PS_3$: C, 42.74; H, 5.74; N, 9.97. Found; C, 42.99; H, 5.98; N, 9.93.

Methyl N-[[[[[ethyl(phenoxy)phosphinothioyl]anilino]thio]methylamino]carbonyl]oxy]ethanimidothioate, m.p. 74° to 76° C.

Analysis: Calc'd for $C_{18}H_{24}N_3O_3PS_3$: C, 48.60; H, 5.14; N, 8.95. Found; C, 48.74; H, 4.98; N, 9.03

Methyl N-[[[[[4-chlorophenoxy(ethyl)phosphinothioyl]isopropylamino]thio]methylamino]carbonyl]oxy]ethanimidothioate, m.p. 65° to 66° C.

Analysis: Calc'd for $C_{16}H_{25}ClN_3O_3S_3P$: C, 40.89; H, 5.36; N, 8.94; Cl, 7.54. Found; C, 41.08; H, 5.48; N, 9.14; Cl, 7.62.

Methyl N-[[[[[methyl(isopropoxy)phosphinothioyl]anilino]thio]methylamino]carbonyl]oxy]ethanimidothioate, m.p. 76° to 78° C.

Analysis: Calc'd for $C_{15}H_{24}N_3O_3PS_3$: C, 42.73; H, 5.74; N, 9.97. Found; C, 42.68; H, 5.92; N, 10.02.

Methyl N-[[[[[([1,1'-biphenyl]-4-yloxy)ethylphosphinothioyl]isopropylamino]thio]methylamino]carbonyl]oxy]ethanimidothioate as a pale yellow oil.

Analysis: Calc'd for $C_{22}H_{30}N_3O_3PS_3$: C, 51.64; H, 5.91; N, 8.21. Found; C, 52.00; H, 6.10; N, 8.04.

Methyl N-[[[[[phenyl(phenoxy)phosphinothioyl]ethylamino]thio]methylamino]carbonyl]oxy]ethanimidothioate. White crystals, m.p. 122° to 123° C.

Analysis: Calc'd for $C_{17}H_{24}N_3O_3PS_3$ C, 48.60; H, 5.15; N, 8.95. Found; C, 48.56; H, 5.23; N, 9.04.

Methyl N-[[[[[ethyl(phenoxy)phosphinothioyl]benzylamino]thio]methylamino]carbonyl]oxy]ethanimidothioate obtained as pale yellow oil.

Analysis: Calc'd for $C_{20}H_{26}N_3O_3PS_3$: C, 49.67; H, 5.42; N, 8.69. Found; C, 49.64; H, 7.19; N, 8.41.

Methyl N-[[[[[ethyl(phenoxy)phosphinothioyl]4-chloroanilino]thio]methylamino]carbonyl]oxy]ethanimidothioate. White crystals, m.p. 69° to 71° C.

Analysis: Calc'd for $C_{19}H_{23}ClN_3O_3PS_3$: C, 45.28; H, 4.60; N, 8.34. Found; C, 47.62; H, 5.12; N, 8.00.

Methyl N-[[[[[ethoxy(phenyl)phosphinothioyl]benzylamino]thio]methylamino]carbonyl]oxy]ethanimidothioate obtained as a yellow viscous oil.

Analysis: Calc'd for $C_{20}H_{26}N_3O_3PS_3$: C, 49.67; H, 5.42; N, 8.69. Found; C, 46.43; H, 5.07; N, 7.80.

Methyl N-[[[[[ethyl(phenoxy)phosphinothioyl]n-butylamino]thio]methylamino]carbonyl]oxy]ethanimidothioate, obtained as a yellow oil.

Analysis: Calc'd for $C_{17}H_{28}N_3O_3PS_3$: C, 45.42; H, 6.28; N, 9.35. Found; C, 45.46; H, 6.42; N, 8.62.

Methyl N-[[[[[2-chlorophenoxy(ethyl)phosphinothioyl]anilino]thio]methylamino]carbonyl]oxy]ethanimidothioate, obtained as a yellow oil.

Analysis: Calc'd for $C_{19}H_{23}ClN_3O_3PS_3$: C, 45.28; H, 4.60; N, 8.34; Cl, 7.03. Found; C, 45.81; H, 4.74; N, 8.38; Cl, 7.44.

Methyl N-[[[[[4-chlorophenoxy(ethyl)phosphinothioyl]anilino]thio]methylamino]carbonyl]oxy]ethanimidothioate. White crystals, m.p. 60° to 62° C.

Analysis: Calc'd for $C_{19}H_{23}ClN_3O_3PS_3$: C, 45.28; H, 4.60; N, 8.34; Cl, 7.03. Found; C, 46.25; H, 4.92; N, 7.87; Cl, 6.88.

Methyl N-[[[[[ethyl(phenoxy)phosphinothioyl]cyclohexylamino]thio]methylamino]carbonyl]oxy]ethanimidothioate, white crystals, m.p. 129° to 130° C.

Analysis: Calc'd for $C_{19}H_{30}N_3O_3PS_3$: C, 47.98; H, 6.36; N, 8.83. Found; C, 48.14; H, 6.57; N, 8.94.

Methyl N-[[[[[ethyl(phenoxy)phosphinothioyl]-p-nitroanilino]thio]methylamino]carbonyl]oxy]ethanimidothioate.

Methyl N-[[[[[ethyl(phenoxy)phosphinothioyl]-o-methylanilino]thio]methylamino]carbonyl]oxy]ethanimidothioate.

Methyl N-[[[[[ethyl(phenoxy)phosphinothioyl]-m-trifluoromethylanilino]thio]methylamino]carbonyl]oxy]ethanimidothioate.

Methyl N-[[[[[ethyl(phenoxy)phosphinothioyl]-o-chloroanilino]thio]methylamino]carbonyl]oxy]ethanimidothioate.

Methyl N-[[[[[cyclohexyloxy(ethyl)phosphinothioyl]cyclohexylamino]thio]methylamino]carbonyl]oxy]ethanimidothioate.

Methyl N-[[[[[ethyl(p-nitrophenoxy)phosphinothioyl]anilino]thio]methylamino]carbonyl]oxy]ethanimidothioate.

Methyl N-[[[[[ethoxy(phenyl)phosphinothioyl]anilino]thio]methylamino]carbonyl]oxy]ethanimidothioate.

EXAMPLE 6

Starting with the appropriate O-[[methylamino]carbonyl]oxime of 2-alkyl-1,3-dithiolane-2-carboxaldehydes and the appropriate phosphoramidothioates, the following compounds are prepared by procedures similar to Example 2, Part B.

2-Methyl-1,3-dithiolane-2-carboxaldehyde, O-[[[[diethoxyphosphinothioyl]anilino]thio]methylcarbamoyl]oxime.

2-Methyl-1,3-dithiolane-2-carboxaldehyde, O-[[[[diethoxyphosphinothioyl]methylamino]thio]methylcarbamoyl]oxime.

2-Methyl-1,3-dithiane-2-carboxaldehyde, O-[[[[phenoxy(phenyl)phosphinothioyl]ethylamino]thio]methylcarbamoyl]oxime.

2-Methyl-1,3-dithiane-2-carboxaldehyde, O-[[[[diethoxyphosphinothioyl]anilino]thio]methylcarbamoyl]oxime.

2-Ethyl-1,3-dithiane-2-carboxaldehyde, O-[[[[diethoxyphosphinothioyl]anilino]thio]methylcarbamoyl]oxime.

2-Ethyl-1,3-dithiane-2-carboxaldehyde, O-[[[[ethoxy(phenoxy)phosphinothioyl]methylamino]thio]methylcarbamoyl]oxime.

2-Methyl-1,3-dithiane-2-carboxaldehyde O-[[[[ethoxy(thiophenoxy)phosphinothioyl]methylamino]thio]methylcarbamoyl]oxime.

2-Methyl-1,3-dithiane-2-carboxaldehyde, O-[[[[diethoxyphosphinoyl]anilino]thio]methylcarbamoyl]oxime.

EXAMPLE 7

Starting with the known compound O-[[methylamino]carbonyl]oxime of 1,3-Dithiolane-2-one and the appropriate phosphoramidothioates, the following compounds are prepared by procedures similar to Example 2, Part B.

1,3-Dithiolane-2-one, O-[[[[diethoxyphosphinothioyl]methylamino]thio]methylcarbamoyl]oxime.

1,3-Dithiolane-2-one, O-[[[[diethoxyphosphinyl]methylamino]thio]methylcarbamoyl]oxime.

1,3-Dithiolane-2-one, O-[[[[diethoxyphosphinothioyl]anilino]thio]methylcarbamoyl]oxime.

1,3-Dithiolane-2-one, O-[[[[phenoxy(phenyl)phosphinothioyl]methylamino]thio]methylcarbamoyl]oxime.

1,3-Dithiolane-2-one, O-[[[[phenoxy(phenyl)phosphinothioyl]ethylamino]thio]methylcarbamoyl]oxime.

EXAMPLE 8

Starting with the known compound 2,3-dihydro-2,2-dimethyl-7-benzofuranyl methylcarbamate and the appropriate phosphoramidothioates, the following compounds are prepared by procedures similar to Example 2, Part B.

2,3-Dihydro-2,2-dimethyl-7-benzofuranyl [[[diethoxyphosphinothioyl]methylamino]thio]methylcarbamate.

2,3-Dihydro-2,2-dimethyl-7-benzofuranyl [[[ethyl(phenoxy)phosphinothioyl]methylamino]thio]methylcarbamate.

2,3-Dihydro-2,2-dimethyl-7-benzofuranyl [[[diethoxyphosphinothioyl]ethylamino]thio]methylcarbamate.

2,3-Dihydro-2,2-dimethyl-7-benzofuranyl [][diethylphosphinothioyl]methylamino]thio]methylcarbamate.

2,3-Dihydro-2,2-dimethyl-7-benzofuranyl [[[ethoxy(phenyl)phosphinothioyl]anilino]thio]methylcarbamate.

2,3-Dihydro-2,2-dimethyl-7-benzofuranyl [[[ethoxy(ethyl)phosphinothioyl]methylamino]thio]methylcarbamate.

2,3-Dihydro-2,2-dimethyl-7-benzofuranyl [[[ethyl(thiophenoxy)phosphinothioyl]methylamino]thio]methylcarbamate.

2,3-Dihydro-2,2-dimethyl-7-benzofuranyl [[[p-chlorophenyl(methyl)phosphinothioyl]methylamino]thio]methylcarbamate.

2,3-Dihydro-2,2-dimethyl-7-benzofuranyl [[[diethoxyphosphinyl]methylamino]thio]methylcarbamate.

2,3-Dihydro-2,2-dimethyl-7-benzofuranyl [[[ethyl(phenoxy)phosphinyl]methylamino]thio]methylcarbamate.

2,3-Dihydro-2,2-dimethyl-7-benzofuranyl [[[phenoxy(phenyl)phosphinyl]methylamino]thio]methylcarbamate.

2,3-Dihydro-2,2-dimethyl-7-benzofuranyl [[[ethoxy(ethyl)phosphinyl]anilino]thio]methylcarbamate.

2,3-Dihydro-2,2-dimethyl-7-benzofuranyl [[[methyl(thiophenoxy)phosphinyl]anilino]thio]methylcarbamate.

EXAMPLE 9

Methyl N-[[[[[(5,5-dimethyl-2-thioxo-1,3,2-dioxaphosphorinan-2-yl)isopropylamino]thio]methylamino]carbonyl]oxy]ethanimidothioate.

A solution of 5,5-dimethyl-2-isopropylamino-2-thioxo-1,3,2-dioxaphosphorinane (3.00 g, 13.4 mmol) and triethylamine (1.9 ml, 13.5 mmol) in tetrahydrofuran (20 ml) is added dropwise over 20 minutes to a stirred solution of sulfur dichloride (1.00 ml, 15.7 mmol) in tetrahydrofuran (20 ml) at room temperature. Following the addition the mixture is stirred at room temperature for 1 hour. Cuprous chloride (0.25 g) is added to the mixture followed by dropwise addition of a solution of Methyl N-[[(methylamino)carbonyl]oxy]ethanimidothioate (2.17 g, 13.4 mmol) and triethylamine (1.90 ml, 13.5 mmol) in tetrahydrofuran (20 ml.). The mixture is stirred for two hours at room temperature then diluted with water and extracted with ethyl acetate. The organic phase is washed with water, dried over magnesium sulfate, and concentrated under reduced pressure. The residual oil is chromatographed over silica gel eluting with a mixture of ethyl acetate - Skellysolve B in the ratio of 2 to 3. The chromatographed product is recrystallized from ethyl acetate, to give Methyl N-[[[[[(-5,5-dimethyl-2-thioxo-1,3,2-dioxaphosphorinan-2-yl)isopropylamino]thio]methylamino]carbonyl]oxy]ethanimidothioate as a white solid of melting point 114°–115° C. The nmr and ir spectra are consistent with the expected structure.

Analysis: Calc'd for $C_{13}H_{26}N_3O_4PS_3$: C, 37.58; H, 6.31; N, 10.11 Found; C, 37.63; H, 6.25; N, 10.11.

EXAMPLE 10

Methyl N-[[[[[(5,5-dimethyl-2-thioxo-1,3,2-dioxaphosphorinano-2-yl)tert-butylamino]thio]methylamino]carbonyl]oxy]ethanimidothioate A solution of 7.4 g (31 mmol) of 2-tert-butylamino-5,5-dimethyl-2-thioxo-1,3,2-dioxaphosphorinane and 4.4 ml of triethylamine (31 mmol) in 50 ml of tetrahydrofuran is added dropwise over 20 minutes with stirring to a solution of 2.0 ml sulfur dichloride (31 mmol) in 20 ml of tetrahydrofuran cooled to 0° C. After the addition the mixture is stirred for 30 minutes at 0° C. Cuprous chloride (0.3 g) is added to the mixture followed by dropwise addition over 20 minutes of a solution of 5.1 g. (31 mmol) of methyl N-[[(methylamino)carbonyl]oxy]ethanimidothioate and 4.4 ml of triethylamine (31 mmol) in 50 ml of tetrahydrofuran. After the addition the mixture is stirred for 2 hours allowing to warm to room temperature. The mixture is diluted with ethyl acetate and washed with water. The organic solution is dried over magnesium sulfate and concentrated under reduced pressure. The residue is treated with a 1 to 2 mixture of ether-hexane to precipitate a crude product. Two recrystallizations from methanol gives analytically pure material of mp 167°–168.5° C. The nmr and ir spectra are consistent with the expected structure.

Analysis: Calc'd. for $C_{14}H_{28}N_3O_4PS_3$: C, 39.14; H, 6.57; N, 9.78. Found: C, 39.45; H, 6.73; N, 9.87.

EXAMPLE 11

Methyl N-[[[[[cyclohexyl(5,5-dimethyl-2-thioxo-1,3,2-dioxaphosphorinan-2-yl)amino]thio]methylamino]carbonyl]oxy]ethanimidothioate A solution of 12.4 g 2-cyclohexylamino-5,5-dimethyl-2-thioxo:1,3,2-dioxaphosphorinane and 6.55 ml triethylamine in 50 ml tetrahydrofuran is added with stirring over 15 minutes to a solution of 3.0 ml sulfur dichloride in 50 ml. tetrahydrofuran cooled to −5° to 0° C. After the addition the mixture is stirred at 0° for 45 minutes when 0.20 g of cuprous chloride is added. A solution of 7.67 g methyl N-[[(methylamino)carbonyl]oxy]ethanimidothioate and 6.55 ml triethylamine in 50 ml tetrahydrofuran is added over 15 minutes. After the addition the mixture is stirred and allowed to warm to room temperature over 75 minutes. The mixture is diluted with water and extracted with ethyl acetate. The extracts are washed with water, dried over magnesium sulfate and concentrated under reduced pressure. Recrystallization of the semi-solid residue from ethyl acetate-hexane affords 9.36 g of the methyl N-[[[[[cyclohexyl(5,5-dimethyl-2-thioxo-1,3,2-dioxaphosphorinan-2-yl)amino]thio]methylamino]carbonyl]oxy]ethanimidothioate as a white solid, m.p. 138°–140d° C.

Analysis Calc'd for $C_{16}H_{30}N_3O_4PS_3$: C, 42.18; H, 6.64; N, 9.22. Found: C, 42.39; H, 6.71; N, 9.32.

The nmr and ir spectra are consistent with the expected structure.

EXAMPLE 12

Methyl N-[[[[[isopropyl(5,5-diethyl-2-thioxo-1,3,2-dioxaphosphorinan-2-yl)amino]thio]methylamino]carbonyl]oxy]ethanimidothioate A solution of 10.94 g of 5,5-diethyl-2-isopropylamino-2-thioxo-1,3,2-phosphorinane and 6.05 ml of triethylamine in 50 ml tetrahydrofuran is added dropwise over 15 minutes to a solution of 2.72 ml of sulfur dichloride in 50 ml tetrahydrofuran, cooled to −5° to 0° C. After the addition, the mixture is stirred for 1 hour at 0° when 0.10 g of cuprous chloride is added. A solution of 7.06 g of methyl N-[[(methylamino)carbonyl]oxy]ethanimidothioate and 6.05 ml triethylamine in 50 ml tetrahydrofuran is added dropwise over 15 minutes. The mixture is stirred and allowed to warm to room temperature over 1 hour when it is diluted with water and extracted with ethyl acetate. The extracts are washed with water, dried over magnesium sulfate and concentrated under reduced pressure. The residual oil is chromatographed over silica gel using a 1 to 1 mixture of ethyl acetate and hexane to afford the product. Recrystallization from ethyl acetate-hexane gives methyl N-[[[[[isopropyl(5,5-diethyl-2-thioxo-1,3,2-phosphorinan-2-yl)amino]thio]methylamino]carbonyl]oxy]ethanimidothioate as a white solid, m.p. 123°–124.5° C.

Analysis Calc'd for $C_{15}H_{30}N_3O_4PS_3$: C, 40.61; H, 6.82; N, 9.48. Found: C, 40.83; H, 6.91; N, 9.60.

The pmr and ir spectra are consistent with the expected structure.

EXAMPLE 13

Starting with the appropriate methylcarbamates and phosphoramidothioates and utilizing a procedure similar to Example 10 the following compounds are prepared.

Methyl N-[[[[[isopropyl(2-thioxo-1,3,2-phospholan-2-yl)amino]thio]methylamino]carbonyl]oxy]ethanimidothioate, m.p. 120°–122° C.

Analysis Calc'd for $C_{10}H_{20}N_3O_4PS_3$: C, 32.16; H, 5.40; N, 11.25. Found: C, 32.17; H, 5.31; N, 11.49.

Methyl-[[[[[cyclohexyl(5,5-diethyl-2-thioxo-1,3,2-dioxaphosphorinan-2-yl)amino]thio]methylamino]carbonyl]oxy]ethanimidothioate, m.p. 155°–157° C.

Analysis Calc'd for $C_{18}H_{34}N_3O_4PS_3$: C, 44.70; H, 7.09; N, 8.69. Found: C, 44.96; H, 7.11; N, 8.81.

Methyl-[[[[[isopropyl(2-thioxo-1,3,2-dioxaphosphorinan-2-yl)amino]thio]methylamino]carbonyl]oxy]ethanimidothioate, m.p. 153°–154° C.

Analysis Calc'd for $C_{11}H_{22}N_3O_4PS_3$: C, 43.10; H, 5.72; N, 10.84. Found: C, 34.21; H, 5.87; N, 11.13.

Methyl-[[[[[ethyl(5,5-dimethyl-2-thioxo-1,3,2-dioxaphosphorinan-2-yl)amino]thio]methylamino]carbonyl]oxy]ethanimidothioate, m.p. 111°–112° C.

Calc'd for $C_{12}H_{24}N_3O_4PS_3$: C, 35.90; H, 6.03; N, 10.47 Found: C, 36.13; H, 6.22; N, 10.26.

Methyl N-[[[[[isopropyl(4,4,6-trimethyl-2-thioxo-1,3,2-dioxaphosphorinan-2-yl)amino]thio]methylamino]carbonyl]oxy]ethanimidothioate, m.p. 123°–7° C.

Calc'd for $C_{14}H_{27}N_3O_4PS_3$: C, 39.24; H, 6.35; N, 9.80. Found: C, 39.76; H, 6.94; N, 9.76.

methyl N-[[[[[(2-thioxo-4H-1,3,2-benzodioxaphosphorin-2-yl)isopropylamino]thio]methylamino]carbonyl]oxy]ethanimidothioate;

methyl N-[[[[[(2-thioxo-1,3,2-dioxaphospholan-2-yl)methylamino]thio]methylamino]carbonyl]oxy]ethanimidothioate;

methyl N-[[[[[ethyl(hexahydro-2-oxo-1,3,2-benzodioxaphospholan-2-yl)amino]thio]methylamino]carbonyl]oxy]ethanimidothioate;

methyl N-[[[[[isopropyl(2-oxo-1,3,2-benzodioxaphospholan-2-yl)amino]thio]methylamino]carbonyl]oxy]ethanimidothioate;

methyl N-[[[[[benzyl(5,5-diethyl-2-thioxo-1,3,2-dioxaphosphorinan-2-yl)amino]thio]methylamino]carbonyl]oxy]ethanimidothioate;

methyl N-[[[[[methyl(2-thioxo-1,3,2-dioxaphosphorinan-2-yl)amino]thio]methylamino]carbonyl]oxy]ethanimidothioate, 94°–96° C.

The compounds of formula I, I', I" and I''' are effective pesticides that can be used to control invertebrate pests in agriculture, industry, and around the home. The compounds have been compared with the precursor methylcarbamates.

Representative pest species have been used, illustratively, order Lepidoptera, more specifically, the southern armyworm (SAW), (*Prodenia eridania* Cramer), the tobacco budworm (TBW), (*Heliothis virescens*), and the cabbage looper (CL) (*Trichoplusia ni*); order Acarina, more specifically, the two-spotted spider mite (TSSM) (*Tetranychus urticae* Koch); order Diptera, more specifically, the housefly (HF) (*Musca domestica* Linnaeus) or the yellow-fever mosquito (YFM) (*Aedes aegypti*); order Orthoptera, more specifically, the house cricket (HC) (*Acheta domesticus* Linnaeus) or the German cockroach (GC) (*Blatella germanica* Linnaeus); order Coleoptera, more specifically, the cotton boll weevil (BW) (*Anthonomus grandis* Boheman).

Efficacy against invertebrate pests has been demonstrated at concentrations as low as 0.5 ppm, depending upon the specific pest used. Some invertebrate animal pests will be more sensitive to the compounds than others, and others might be quite resistant. In general, the compounds of Formula I are used at concentrations ranging from about 30 to about 6000 ppm.

In general, the compounds exhibit the mortality activity of the parent methylcarbamate while at the same time exhibiting both lower toxic and phytotoxic effects. Mammalian Toxicity is given.

4-(Dimethylamino)-3,5-xylyl[[(diethoxyphosphino-sphinothiol]-n-propylamino]thio]methylcarbamate

| Insect | Rate | Mortality |
|---|---|---|
| SAW | 100 ppm | 100 |
| YFM | 0.6 ppm | 100 |

Methyl N-[[[[[(diethoxyphosphinothioyl)iso-propylamino]thiol]methylamino]carbonyl]oxy]ethan-imidothioate

| Insect | Rate | Mortality |
|---|---|---|
| SAW | 3.3 ppm | 100 |
| CL | 3.3 ppm | 100 |
| BW | 50 ppm | 60 |
| HF | 25 ppm | 80 |
| YFM | 1.0 ppm | 100 |

Methyl N-[[[[[(methoxy(phenyl)phosphinothioyl)iso-propylamino]thio]methylamino]carbonyl]oxy]ethani-midothioate

| Insect | Rate | Mortality |
|---|---|---|
| SAW | 3.3 ppm | 90 |
| CL | 3.3 ppm | 50 |
| HF | 25 ppm | 50 |
| BW | 25 ppm | 80 |

Methyl N-[[[[[(cyclohexyl (5,5-dimethyl-2-thioxo-1,3,2-dioxa-phosphorinan-2-yl)amino]thio]methylamino]carbonyl]oxy]ethanimido-thioate

| Insect | Rate | Mortality |
|---|---|---|
| SAW | 11 ppm | 70 |
| CL | 11 ppm | 87.5 |
| TBW | 11 ppm | 95 |

Mammalian Toxicity - Oral LD$_{50}$, Rat > 8000 mg/kg

Methyl N-[[[[[isopropyl(5,5-diethyl-2-thioxo-1,3,2-dioxaphosphorinan-2-yl)amino]thio]methylamino]carbonyl]oxy]ethanimidothioate

| Insect | Rate | Mortality |
|---|---|---|
| SAW | 11 ppm | 60 |
| CL | 11 ppm | 95 |
| TB | 11 ppm | 100 |

Mammalian Toxicity Oral LD$_{50}$, Rat > 2000 mg/kg

Methyl N-[[[[[isopropyl(2-thioxo-1,3,2-phospholan-2-yl)amino]thio]-methylamino]carbonyl]oxy]ethanimidothioate, m.p. 120°-122° C.

| Insect | Rate | Mortality |
|---|---|---|
| SAW | 11 ppm | 40 |
| CL | 11 ppm | 48 |
| TB | 11 ppm | 45 |

Methyl N-[[[[[cyclohexyl(5,5-diethyl-2-thioxo-1,3,2-dioxaphosphorine nan-2-yl)amino]thio]methylamino]carbonyl]oxy]ethanimidothioate, m.p. 155°-157° C.

| Insect | Rate | Mortality |
|---|---|---|
| SAW | 11 ppm | 70 |
| CL | 11 ppm | 77.5 |
| TB | 11 ppm | 95 |

Mammalian Toxicity Oral LD$_{50}$, Rat > 8000

Methyl N-[[[[[isopropyl(2-thioxo-1,3,2-dioxaphosphorinan-2-yl)-amino]thio]methylamino]carbonyl]oxy]ethanimidothioate, m.p. 153°-154° C.

| Insect | Rate | Mortality |
|---|---|---|
| SAW | 11 ppm | 56 |
| CL | 11 ppm | |
| TB | 11 ppm | |

Methyl N-[[[[[ethyl(5,5-dimethyl-2-thioxo-1,3,2-dioxaphosphorinan-2-yl)amino]thio]methylamino]carbonyl]oxy]ethanimidothioate, m.p. 111°-112° C.

| Insect | Rate | Mortality |
|---|---|---|
| | -continued | |
| Insect | Rate | Mortality |
| CL | 11 ppm | 56 |

Methyl N-[[[[[isopropyl(4,4,6-trimethyl-2-thioxo-1,3,2-dioxaphosphori-nan-2-yl)amino]thio]methylamino]carbonyl]oxy]ethanimidothioate, m.p. 123°-7° C.

| Insect | Rate | Mortality |
|---|---|---|
| CL | 11 ppm | 92.5 |

The details of the mortality tests are as follows:

Preparation of tested chemicals—Analytical samples of each were dissolved in acetone. These acetone solutions were applied as such or portions of them were diluted with a Tween 20 "wet water" or a 10% sucrose "wet water". The "wet water" itself contained 0.132% v/v of Tween 20 (polyoxyethylene sorbitan monolaurate).

The southern armyworm and cabbage looper tests were effected with Henderson bush lima bean foliage characterized by two primary leaves per replicate. The leaves were dipped into a "wet water" emulsion of a test chemical, allowed to dry, and then placed on a moistened filter disk in a 9 cm plastic petri dish. Five larva of the respective test insects were put on the leaves, the cover of the petri dish was replaced, and it was set aside for future evaluation. Three replications for each treatment rate were prepared.

The house cricket test was effected by pipetting 5 ml portions of the acetone solutions into 9 cm petri dishes and allowing the acetone to evaporate. Ten nymphal house crickets were released into the treated dish and the cover was replaced. Three replicates for each treatment rate were prepared.

The house fly and boll weevil tests were effected by saturating a golf-ball size wad of cotton with 10 ml of a "10% wet sugar water" preparation of the test chemical. The saturated wad was placed in a portion cup which was attached to the inside surface of a 5-ounce waxed paper cup. Ten adult house flies or boll weevils were released in the 5-ounce cup and it was covered with a plastic lid for future observation. Two replicates were prepared for each treatment rate.

The yellow fever mosquito larvae test was effected by adding the appropriate amount of a wet water and acetone solution of the test chemical to 100 ml distilled water in a 5-ounce waxed paper cup. Ten mosquito larvae were added. Dried yeast was added after twenty-four hours. There were two replicates for each treatment rate.

The southern armyworm, house cricket, boll weevil, house fly, and cabbage looper tests were held at 22° C., while the yellow fever mosquito larvae tests were held at 27° C.

The tests were evaluated for insect kill (including moribund and knocked down) after 24, 48, and sometimes 72 hours.

In other tests, the phytotoxicity, residual effectiveness, and animal toxicity of e.g. Methyl N-[[[[[(diethoxyphosphinothioyl)isopropylamino]thio]methylamino]carbonyl]oxy]ethanimidothioate were compared with the parent compound, methyl N-[[(methylamino)carbonyl]oxy]ethanimidothioate. Utilizing a scale on which 0 represents no damage and 10 represents complete kill of plant, this new derivative was in general less phytotoxic than the parent, and markedly less phytotoxic on the sensitive crop, eggplant. Illustratively, the new derivative had an average phytotoxicity index of about 1.0 and 1.5 at a concentration of 300 and 600 parts per million (ppm), respectively after eight days. The parent compound had corresponding index values of 4.25 and 5.0.

These compounds were also compared for their foliar residual effectiveness against southern armyworm larvae on lima bean seedlings. The compound Methyl N-[[[[[(diethoxyphosphinothioyl)isopropylamino]thio]methylamino]carbonyl]oxy]ethanimidothioate of this invention was producing 100 percent mortality seven weeks after the treatment was applied, whereas the activity of the parent compound at an equivalent rate had dissipated to 20% by the 14th day.

In a comparison for oral toxicity to male rats, the compound, methyl N-[[[[[(diethoxyphosphinothioyl)isopropylamino]thio]methylamino]carbonyl]oxy]ethanimidothioate has been shown to be less than one fourth as toxic as the parent methylcarbamate. The acute, oral $LD_{50}$'s are 105 mg/kg of body weight and 17-24 mg/kg of body weight respectively.

As pointed out above, the compounds of Formula Ia are particularly effective. Illustratively, the compound methyl N-[[[[[ethyl(phenoxy)phosphinothioyl]anilino]thio]methylamino]carbonyl]oxy]ethanimidothioate shows up to three times the insecticidal activity of the parent compound, methyl N-[[(methylamino)carbonyl]oxy]ethanimidothioate (methomyl) against lepidopterous species; for example, southern army worm (SAW) and cabbage looper.

The foregoing test results indicate that the objectives of the invention have been satisfied and that a worthwhile contribution has been made to the pesticide art. They further indicate that the N-[(phosphinyl)amino]thio and N-[(phosphinothioyl)amino]thiomethylcarbamates of this invention can be utilized for control of insect pests in the form of the pure compounds as prepared in the Examples, as technical grade compounds from commercial production, or as mixtures of the specific compounds. On the other hand, practical considerations indicate the desirability of providing those skilled in the pesticide art with formulations comprising a diluent carrier with or without adjuvants that will promote the distribution of the active compounds where pest control is desired and thus enhance efficacy and economics.

There are many different kinds of diluent carriers suitable for the method and formulation embodiments of this invention. Dispersible carriers are commonly used in the art. Such carriers may or may not include adjuvants such as wetting agents, emulsifying agents, stickers, and other components that indirectly promote efficacy.

The new carbamates of Formula 1, 1', 1" and 1''' are useful against insects, nematodes, and mites in formulations, e.g. as dusts, wettable powders, emulsifiable concentrates, aqueous dispersions, solutions, and flowable creams for application to a situs, soil, plants, and foliage, seeds, or other parts of plants. Granular formulations can be prepared and applied to soil or on surfaces. Moreover, the new compounds of Formula (1, 1', 1" and 1''') of this invention can be the sole active agent in a formulation or other insecticidal, miticidal, or nematicidal components may be included.

The new solid compounds of Formula 1, 1', 1" and 1''' can be readily formulated as dusts by grinding a mixture of the compound and a pulverulent carrier in the presence of each other. Grinding is conveniently accomplished in a ball mill, a hammermill, or by air-blast micronization. A suitable ultimate particle size is less than 60 microns. Preferably, 95% of the particles are less than 50 microns, and about 75% are 5 to 20 microns. Dusts of that degree of comminution are conveniently free-flowing and can be applied to animals, inanimate matter, fruit trees, crop plants, and soil so as to effect thorough distribution and coverage. Dusts are particularly adapted for effectively controlling insects and mites over wide areas when applied by airplane. They are also indicated for application to the undersides of plant foliage.

Representative suitable pulverulent carriers include the natural clays such as China, Georgia, Barden, Attapulgus, Kaolin, and Bentonite clays; minerals in their natural forms as they are obtained from the earth such as talc, pyrophillite, quartz, diatomaceous earth, Fuller's earth, chalk, sulfur, silica and silicates; chemically modified minerals such as washed bentonite and colloidal silica; and organic flours such as wood, walnut shell, soybean, cottonseed, and tobacco flours, and free-flowing, hydrophobic starches.

Dusts can also be prepared by dissolving the phosphinic acid derivatives of aminothio methylcarbamate pesticides of Formulas 1, 1', 1" and 1''' in a volatile solvent such as methylene chloride, mixing the solution with a pulverulent carrier and evaporating the solvent.

The proportions of pulverulent carrier and active compound (Formula 1, 1', 1" and 1''') can vary over a wide range depending upon the use of it, nematode or mite pests to be controlled, and the conditions of treatment. In general, dust formulations can contain up to about 90% (on a weight basis) of the active ingredient.

The dispersible powder formulations of this invention are prepared by incorporating a surfactant in a dust formulation prepared as described above. When about 0.1% to about 12% of a surfactant is incorporated in a dust, the dispersible powder thus obtained is particularly adapted for further admixture with water for spraying on inanimate matter and products, fruit trees, field crops, soil, and livestock. The dispersible powders can be admixed with water to obtain any desired concentration of active ingredient, and the mixture can be applied in amounts sufficient to obtain predetermined rates of application and uniform distribution. With this flexibility in mind, the dispersible powders of the invention can conveniently comprise preferably about 5% to about 80% of active ingredient.

Representative surfactants useful for preparing dispersible powder formulations of this invention include alkyl sulfates and sulfonates, alkyl aryl sulfonates, sulfosuccinate esters, polyoxyethylene sulfates, polyoxyethylene sorbitan monolaurate, alkyl aryl polyether sulfates, alkyl aryl polyether alcohols, alkyl naphthalene sulfonates, alkyl quaternary ammonium salts, sulfated fatty acids and esters, sulfated fatty acid amines, glycerol mannitan laurate, polyalkylether condensates of fatty acids, lignin sulfonates, and the like. The preferred class of surfactants includes blends of sulfonated oils and polyalcohol carboxylic acid esters (Emcol H-77), blends of polyethoxy ethanols (Tritons X-151, X-161, X-171), e.g., about equal parts of sodium kerylbenzene sulfonate and isooctylphenoxy polyethoxy ethanol containing about 12 ethoxy groups, and blends of calcium alkyl aryl sulfonates and polyethoxylated vegetable oils (Agrimul $N_2S$). It will be understood, of course, that the sulfate and sulfonate surfactants suggested above will preferably be used in the form of their soluble salts, for example, their sodium salts. All of these surfactants are capable of reducing the surface tension of water in concentrations of about 1% or less. The dispersible powder formulations can be prepared with a mixture of surfactants of the types indicated if desired.

A suitable dispersible powder formulation is obtained by blending and milling 327 lbs. of Georgia Clay, 4.5 lbs. of isooctylphenoxy polyethoxy ethanol (Triton X-100) as a wetting agent, 9 lbs. of a polymerized sodium salt of substituted benzoid long-chain sulfonic acid (Daxad 27) as a dispersing agent, and 113 lbs. of the active ingredient, e.g., the compound embodiment of Example 2. The resulting formulation has the following percentage composition (parts herein are by weight unless otherwise specified).

| Active Ingredient | 25% |
|---|---|
| Isooctylphenoxy polyethoxy ethanol | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied against insects, or mites, on plants, fruit trees, or other habitats, or can be used to spray soil against nematodes.

If desired, dispersants such as methylcellulose, polyvinyl alcohol, sodium ligninsulfonates, and the like can be included in the dispersible powder formulations of this invention. Adhesive or sticking agents such as vegetable oils, naturally occuring gums, casein, Zonarez B, a series of polymerized terpenes, Unicez 709, a maleic acid-derived resin, Polypole, partially dimerized resin acids, and Dymerex, a dimeric resin acid, and others can also be included. Corrosion inhibitors such as epichlorohydrin and anti-foaming agents such as stearic acid can also be included. Methods for including these agents in pesticidal formulation are well-known in the art and are applicable to this invention.

The new compounds of Formula 1, 1', 1" and 1'" of this invention can also be applied to insects, mites, objects, or situs in aqueous sprays without a solid carrier. Since, however, the compounds themselves are relatively insoluble in water, they are preferably dissolved in a suitable inert organic solvent carrier. Advantageously, the solvent carrier is immiscible with water so that an emulsion of the solvent carrier in water can be prepared. If, for example, a water-miscible solvent carrier such as ethanol is used, the solvent carrier will dissolve in the water and any excess of compounds of Formula 1 will be thrown out of the solution. In an oil-in-water emulsion, the solvent phase is dispersed in the water phase and the dispersed phase contains the active ingredient. In this way, uniform distribution of a water insoluble active ingredient is achieved in an aqueous spray. A solvent carrier in which the new compounds of Formula 1 are highly soluble is desirable so that relatively high concentrations of active ingredient can be obtained. Sometimes, one or more solvent carriers with or without a cosolvent can be used in order to obtain concentrated solutions of the active ingredient, the main consideration being to employ a water-immiscible solvent for the active ingredient that will hold the compound in solution over the range of concentrations useful for applying to insects and mites.

The emulsifiable concentrates of the invention are prepared, therefore, by dissolving the active ingredient and a surfactant in a substantially water-immiscible solvent carrier (i.e., a solvent carrier which is soluble in water to the extent of less than 2.5% by volume at temperatures on the order of 20° to 30° C.), for example, cyclohexanone, methyl propyl ketone, summer oils, ethylene dichloride, aromatic hydrocarbons such as benzene, toluene, and xylene, and high-boiling petroleum hydrocarbons such as kerosene, diesel oil, and the like. If desired, a cosolvent such as methyl ethyl ketone, acetone, isopropanol, and the like can be included with a solvent carrier in order to enhance the solubility of the active ingredient. Aqueous emulsions are then prepared by mixing with water to give any desired concentration of active ingredient. The surfactants which can be employed in the aqueous emulsions of the invention are those types noted above. Mixtures of surfactants can be employed, if desired.

Advantageously, the concentration of active ingredient in the emulsifiable concentrates can range from about 5% to about 50% by weight, preferably from about 10% to about 40%. A concentrate comprising 20% (by weight) of the compound dissolved in a water-immiscible solvent of the kind noted above can be admixed with an aqueous medium in the proportions of 13 ml of concentrate with 1 gallon of medium to give a mixture containing 700 parts of active ingredient per million parts of liquid carrier. Similarly, 1 quart of a 20% concentrate mixed with 40 gallons of water provides about 1200 ppm (parts per million) of active ingredient. In the same manner, more consence of desirable living organisms, temperature conditions of treatment, and the method and efficiency of application. In general, insecticidal and miticidal activity is obtained when the compounds are applied at concentrations of about 5 to about 2000 ppm, preferably at concentrations of about 30 to about 1000 ppm. For nematodes from 10 to 50 lbs./acre of the active compound is necessary.

The formulations containing new thio carbamates of Formula 1, 1', 1" and 1'" according to the invention, can be applied to insects, mites, nematodes, soil or other situs by conventional methods. For example, an area of soil, a building, or plants can be treated by applying a wettable powder from a hand-operated knapsack sprayer. Dips can be used for livestock. Dusts can be applied by power dusters, or by hand-operated dusters. Creams and ointment formulations can be applied to skin or objects for prolonged protection from insects or mites.

The active compounds of the invention can also be formulated in relatively dilute proportions in a dispersible insecticide carrier for household applications. Thus, the active compounds can be formulated in dusts having from about 0.1% to 5.0% active ingredient with deodorized kerosene for aerosol applications.

It will, of course, be appreciated that the conditions encountered when applying the method and formulations of this invention to actual practice can vary widely. Included among the variables that may be encountered are the degree of infestation by pests, the particular pest to be controlled, the particular situs being treated, the type of plants, the prevailing weather conditions, such as temperature, relative humidity, rainfall, dews, and so forth.

What is claimed is:

1. N-[(phosphinyl)amino]thio- and N-[(phosphinothioyl)amino]thiomethylcarbamates represented by the schematic formulae

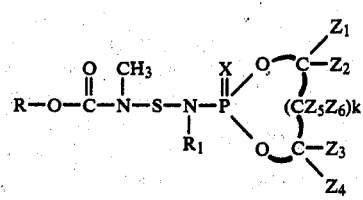

wherein, R is selected from the group consisting of

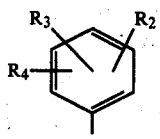

wherein $R_2$, $R_3$, and $R_4$ are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and —N=CHN(CH$_3$)$_2$;

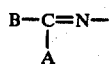

wherein A and B are the same or different and are selected from the group consisting of lower-alkyl of one to five carbon atoms, inclusive, lower-alkylthio of one to five carbon atoms, inclusive, monocyano substituted alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, cyano, alkoxy having one to five carbon atoms, inclusive, phenyl, and hydrogen, with the proviso that when B is hydrogen, A is of the formula

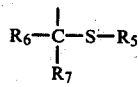

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive and SR$_8$, wherein $R_8$ is alkyl and is the same alkyl group as $R_5$; and taking $R_5$ and $R_8$ together with the atoms to which they are attached form a dithioheterocyclic of the formula

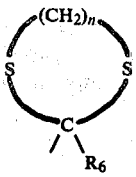

wherein n is 2 or 3 and the alkylene portion of the ring is unsubstituted or substituted with one or two methyl groups; A and B taken together with the carbon atom to which they are attached form a dithio heterocyclic of the formula

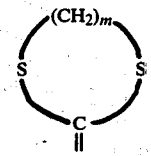

wherein m is 2 or 3 and the alkylene portion of the ring is unsubstituted or substituted with one to two methyl groups;

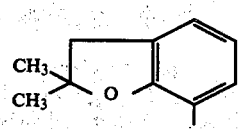

$R_1$ is selected from the group consisting of lower-alkyl, phenyl, substituted phenyl, phenlower-alkyl and cycloalkyl; X is oxygen or sulfur; and $Z_1$ thru $Z_6$ are the same or different and are selected from the group consisting of hydrogen, methyl and ethyl and k is zero or one.

2. Compound according to claim 1 wherein X is sulfur.

3. Compound according to claim 1 wherein X is oxygen.

4. Compound according to claim 2 wherein R is an alkanimido group of the kind

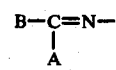

wherein A consists of hydrogen and lower alkyl and B consists of lower alkylthio.

5. A compound according to claim 4 wherein $Z_5$ and $Z_6$ are lower alkyl.

6. A compound according to claim 4 wherein $Z_1$ thru $Z_6$ are hydrogen.

7. A compound according to claim 4 wherein $Z_2$, $Z_5$ and $Z_6$ are lower alkyl.

8. A compound according to claim 5 wherein $R_1$ is lower alkyl.

9. A compound according to claim 6 wherein $R_1$ is lower alkyl.

10. A compound according to claim 7 wherein $R_1$ is lower alkyl.

11. A compound according to claim 5 wherein $R_1$ is cycloalkyl.

12. A compound according to claim 8, methyl N-[[[[(5,5-dimethyl-2-thioxo-1,3,2-dioxaphosphorinan-2- yl)isopropylamino]thio]methylamino]carbonyl]oxy]e-thanimidothioate.

13. A compound according to claim 8, methyl N-[[[[[(5,5-dimethyl-2-thioxo-1,3,2-dioxphosphorinan-2-yl)tert-butylamino]thio]methylamino]carbonyl]oxy]e-thanimidothioate.

14. A compound according to claim 8, methyl N-[[[[[isopropyl(5,5-diethyl-2-thioxo-1,3,2-phosphorinan-2-yl)amino]thio]amino]carbonyl]oxy]ethanimidothioate.

15. A compound according to claim 8, methyl N-[[[[[ethyl(5,5-dimethyl-2-thioxo-1,3,2-dioxaphosphorinan-2-yl)amino]thio]methylamino]carbonyl]oxy]e-thanimidothioate.

16. A compound according to claim 9, methyl N-[[[[[isopropyl(2-thioxo-1,3,2-phospholan-2-yl)amino]-thio]methylamino]carbonyl]oxy]ethanimidothioate.

17. A compound according to claim 9, methyl N-[[[[[isopropyl(2-thioxo-1,3,2-dioxaphosphorinan-2-yl)amino]thio]methylamino]carbonyl]oxy]ethanimido-thioate.

18. A compound according to claim 10, methyl N-[[[[[isopropyl(4,4,6-trimethyl-2-thioxo-1,3,2-dioxaphos-phorinan-2-yl)amino]thio]methylamino]carbonyl]ox-y]ethanimidothioate.

19. A compound according to claim 11, methyl N-[[[[[cyclohexyl(5,5-diethyl-2-thioxo-1,3,2-dioxaphos-phorinan-2-yl)amino]thio]methylamino]carbonyl]ox-y]ethanimidothioate.

20. A compound according to claim 11, methyl N-[[[[[cyclohexyl(5,5-dimethyl-2-thioxo-1,3,2-dioxaphos-phorinan-2-yl)amino]thio]methylamino]carbonyl]ox-y]ethanimidothioate.

21. Methyl N-[[[[[methyl(2-thioxo-1,3,2-dioxaphos-phorinan-2-yl)amino]thio]methylamino]carbonyl]ox-y]ethanimidothioate.

22. The method for controlling insect pests which comprises contacting susceptible insect pests with an effective amount of N-[(phosphinyl)amino]thio- and N-[(phosphinothioyl)amino]thio-methylcarbamates represented by the schematic formula

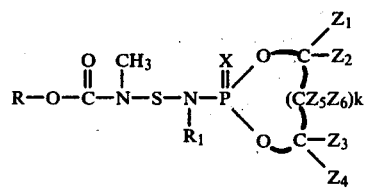

wherein R is selected from the group consisting of

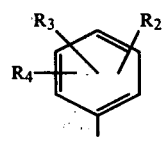

wherein $R_2$, $R_3$, and $R_4$ are the same or different and are selected from the group consisting of hydrogen, lower-alkyl of one to five carbon atoms, inclusive, halogen, lower-alkoxy of one to five carbon atoms, inclusive, halogen, lower-alkylthio of one to five carbon atoms, inclusive, dialkylamino with each alkyl the same or different and having one to three carbon atoms, inclusive, and —N=CHN(CH$_3$)$_2$; and

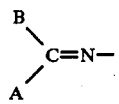

wherein A and B are the same or different and are selected from the group consisting of lower-alkyl of one to five carbon atoms, inclusive, lower-alkylthio of one to five carbon atoms, inclusive, monocyano substituted alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, cyano, alkoxy having one to five carbon atoms, inclusive, phenyl and hydrogen, with the proviso that when B is hydrogen, A is of the formula

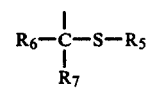

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula

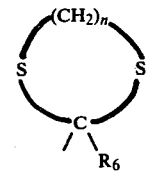

wherein n is 2 or 3 and the alkylene portion of the ring is unsubsituted or substituted with one or two methyl groups; A and B taken together with the carbon atom to which they are attached form a dithio heterocyclic of the formula

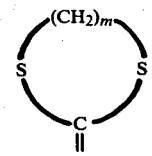

wherein m is 2 or 3 and the alkylene portion of the ring is unsubstituted or substituted with one to two methyl groups; and

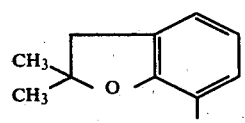

$R_1$ is selected from the group consisting of lower-alkyl, phenyl, substituted phenyl, phenlower-alkyl, and cycloalkyl; X is oxygen or sulfur; and $Z_1$ thru $Z_6$ are the same or different and are selected from the group consisting of hydrogen, methyl and ethyl; and k is zero or one.

23. A method according to claim 22 wherein X is sulfur.

24. A method according to claim 22 wherein X is oxygen.

25. A method according to claim 23 wherein $Z_1$ and $Z_2$ are lower alkyl.

26. A method according to claim 23 wherein $Z_1$ thru $Z_6$ are hydrogen.

27. A method according to claim 23 wherein $Z_1$, $Z_5$ and $Z_6$ are lower alkyl.

28. A method according to claim 25 wherein $R_1$ is lower alkyl.

29. A method according to claim 26 wherein $R_1$ is lower alkyl.

30. A method according to claim 27 wherein $R_1$ is lower alkyl.

31. A method according to claim 25 wherein $R_1$ is cycloalkyl.

32. A method according to claim 28 wherein the compound used is selected from the group consisting of
methyl N-[[[[[(5,5-dimethyl-2-thioxo-1,3,2-dioxaphosphorinan-2-yl)isopropylamino]thio]methylamino]carbonyl]oxy]ethanimidethioate,
methyl N-[[[[[(5,5-dimethyl-2-thioxo-1,3,2-dioxaphosphorinan-2-yl)tert-butylamino]thio]methylamino]carbonyl]oxy]ethanimidothioate,
methyl N-[[[[[isopropyl)5,5-diethyl-2-thioxo-1,3,2-dioxaphosphorinan-2-yl)amino]thio]methylamino]carbonyl]oxy]ethanimidothioate,
methyl N-[[[[[ethyl(5,5-dimethyl-2-thioxo-1,3,2-dioxaphosphorinan-2-yl)amino]thio]methylamino]carbonyl]oxy]ethanimidothioate.

33. A method according to claim 29 wherein the compound used is selected from the group consisting of
methyl N-[[[[[isopropyl(2-thioxo-1,3,2-dioxaphospholan-2-yl)amino]thio]methylamino]carbonyl]oxy]ethanimidothioate, and
methyl N-[[[[[isopropyl(2-thioxo-1,3,2-dioxaphosphorinan-2-yl)amino]thio]methylamino]carbonyl]oxy]ethanimidothioate.

34. A method according to claim 30 wherein the compound used is
methyl N-[[[[[isopropyl(4,4,6-trimethyl-2-thioxo-1,3,2-dioxaphosphorinan-2-yl)amino]thio]methylamino]carbonyl]oxy]ethanimidothioate.

35. A method according to claim 31 wherein the compound used is selected from the group consisting of
methyl N-[[[[[cyclohexyl(5,5-dimethyl-2-thioxo-1,3,2-dioxaphosphorinan-2-yl)amino]thio]methylamino]carbonyl]oxy]ethanimidothioate, and
methyl N-[[[[[cyclohexyl(5,5-diethyl-2-thioxo-1,3,2-dioxaphosphorinan-2-yl)amino]thio]methylamino]carbonyl]oxy]ethanimidothioate.

36. A formula for pest control comprising an adjuvant carrier and a biologically effective amount of one or more N-[(phosphinyl)amino]thio- and N-[(phosphinothioyl)amino]thio- methylcarbamates as active ingredient represented by the schematic formula:

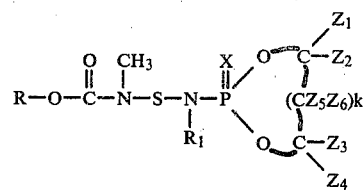

wherein R is selected from the group consisting of

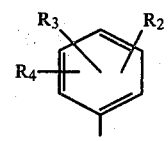

wherein $R_2$, $R_3$, and $R_4$ are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and $N=CHN(CH_3)_2$;

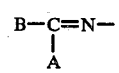

wherein A and B are the same or different and are selected from the group consisting of lower-alkyl of one to five carbon atoms, inclusive, loweralkylthio of one to five carbon atoms, inclusive, monocyano substituted alkylthio of one to five carbon atoms, inclusive, phenylthio wherein phenyl is unsubstituted or substituted with one to three substituents, same or different selected from the group consisting of halogen and lower-alkyl of one to four carbon atoms, inclusive, cyano, alkoxy having one to five carbon atoms, inclusive, phenyl, and hydrogen, with the proviso that when B is hydrogen, A is of the formula

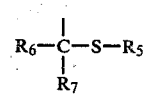

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula

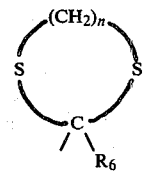

wherein n is 2 or 3 and the alkylene portion of the ring is unsubstituted or substituted with one or two methyl groups; A and B taken together with the carbon atom to which they are attached form a dithio heterocyclic of the formula

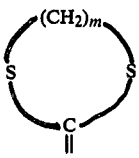

wherein is 2 or 3 and the alkylene portion of the ring is unsubstituted or substituted with one to two methyl groups; and

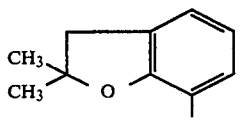

$R_1$ is selected from the group consisting of lower-alkyl, phenyl, substituted phenyl, phenlower-alkyl, and cycloalkyl; X is oxygen or sulfur; and $Z_1$ thru $Z_6$ are the same or different and are selected from the group consisting of hydrogen, methyl and ethyl; and k is zero or one.

37. A formulation according to claim 36 wherein X is sulfur.

38. A formulation according to claim 36 wherein X is oxygen.

39. A formulation according to claim 38 wherein R is an alkanimido group of the kind

wherein A is selected from the group consisting of hydrogen and lower alkyl and B consists of lower alkylthio.

40. A formulation according to claim 39 wherein $Z_5$ and $Z_6$ are lower alkyl.

41. A formulation according to claim 39 wherein $Z_1$ thru $Z_6$ are hydrogen.

42. A formulation according to claim 39 wherein $Z_2$, $Z_5$ and $Z_6$ are lower alkyl.

43. A formulation according to claim 40 wherein $R_1$ is lower alkyl.

44. A formulation according to claim 41 wherein $R_1$ is lower alkyl.

45. A formulation according to claim 42 wherein $R_1$ is lower alkyl.

46. A formulation according to claim 40 wherein $R_1$ is cycloalkyl.

47. A formulation according to claim 43 wherein the active ingredient is selected from the group compounds consisting of specific embodiment is methyl N-[[[[[(5,5-dimethyl-2-thioxo-1,3,2-dioxaphosphorinan-2-yl)isopropylamino]thio]methylamino]carbonyl]oxy]ethanimidethioate, methyl N-[[[[[(5,5-dimethyl-2-thioxo-1,3,2-dioxphosphorinan-2-yl)tert-butylamino]thio]methylamino]carbonyl]oxy]ethanimidothioate, methyl N-[[[[isopropyl(5,5-diethyl-2-thioxo-1,3,2-phosphorinan-2-yl)amino]thio]methylamino]carbonyl]oxy]ethanimidothioate, and methyl N-[[[[[ethyl(5,5-dimethyl-2-thioxo-1,3,2-dioxaphosphorinan-2-yl)amino]thio]methylamino]carbonyl]oxyethanimidothioate.

48. A formulation according to claim 44 wherein the active ingredient is selected from the group of compounds consisting of methyl N-[[[[[isopropyl(2-thioxo-1,3,2-phospholan-2-yl)amino]thio]methylamino]carbonyl]oxy]ethanimidothioate, and methyl N-[[[[[isopropyl(2-thioxo-1,3,2-dioxaphosphorinan-2-yl)amino]thio]methylamino]carbonyl]oxy]ethanimidothioate.

49. A formulation according to claim 45 wherein the active ingredient is methyl N-[[[[[isopropyl(4,4,6-trimethyl-2-thioxo-1,3,2-dioxaphosphorinan-2-yl)amino]thio]methylamino]carbonyl]oxy]ethanimidothioate.

50. A formulation according to claim 46 wherein the active ingredient is selected from the group of compounds consisting of methyl N-[[[[[cyclohexyl(5,5-dimethyl-2-thioxo-1,3,2-dioxaphosphorinan-2-yl)amino]thio]methylamino]carbonyl]oxy]ethanimidothioate and methyl N-[[[[[cyclohexyl(5,5-diethyl-2-thioxo-1,3,2-dioxaphosphorinan-2-yl)amino]thio]methylamino]carbonyl]oxy]ethanimidothioate.

51. A formulation according to claims 47, 48, 49 or 50 wherein the adjuvant carrier is a readily dispersible one.

52. A formulation according to claim 51 wherein the readily dispersible carrier comprises water.

53. A formulation according to claim 52 wherein the formulation further comprises a surface active agent and a finely-divided solid.

54. A formulation according to claim 51 wherein the concentration of active ingredient is from 0.5 percent to 75 percent.

55. N-[(phosphinyl)amino]thio and N-[(phosphinothioyl)amino]thiomethylcarbamates represented by the schematic formula

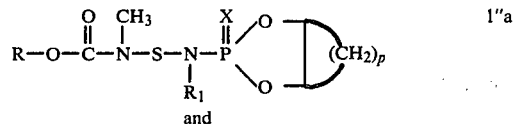

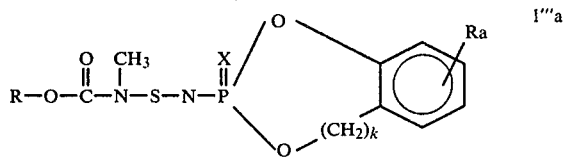

wherein R is selected from the group consisting of

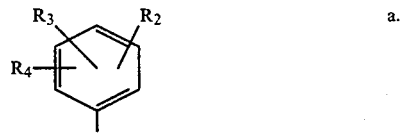

wherein $R_2$, $R_3$, and $R_4$ are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and N=CHN(CH₃)₂;

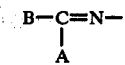
b.

wherein A and B are the same or different and are selected from the group consisting of lower-alkyl of one to five carbon atoms, inclusive, monocyano substituted alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, cyano, alkoxy having one to five carbon atoms, inclusive, phenyl, and hydrogen, with the proviso that when B is hydrogen, A is of the formula

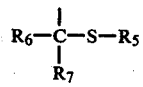

wherein R₅ is selected from the group consisting of alkyl of one to three carbon atoms, inclusive, and phenyl; R₆ is alkyl of one to three carbon atoms, inclusive; R₇ is selected from the group consisting of alkyl of one to three carbon atoms, inclusive, and SR₈, wherein R₈ is alkyl and is the same alkyl group as R₅, and taking R₅ and R₈ together with the atoms to which they are attached form a dithio heterocyclic of the formula

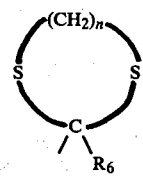

wherein n is 2 or 3 and the alkylene portion of the ring is unsubstituted or substituted with one or two methyl group; A and B taken together with the carbon atom to which they are attached form a dithio heterocyclic of the formula

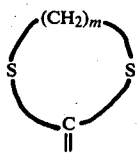

wherein m is 2 or 3 and the alkylene portion of the ring is unsubstituted or substituted with one to two methyl groups; and

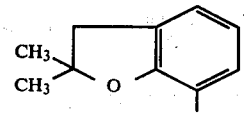

R₁ is selected from the group consisting of lower-alkyl, phenyl, substitute phenyl, phenlower-alkyl and cycloalkyl; X is oxgen or sulfur; P is three or four; Ra is selected from the group consisting of hydrogen, lower alkyl, lower alkoxy, and halogen and k is zero or one.

56. A method for controlling insect pests which comprises contacting susceptible insect pests with an effective amount of a N-[(phosphinyl)amino]thio and N-[(phosphinothioyl)amino]thio-methylcarbamates represented by the schematic formulae

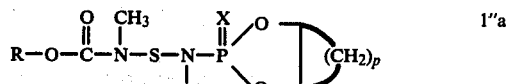
1″a and

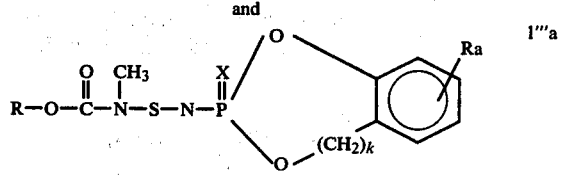
1‴a wherein R is selected from the group consisting of

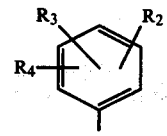
a.

wherein R₂, R₃, and R₄ are the same or different and are selected from the group consisting of hydrogen, lower-alkyl or one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and N=CHN(CH₃)₂;

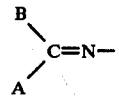

wherein A and B are the same or different and are selected from the group consisting of lower-alkyl or one to five carbon atoms, inclusive, lower-alkylthio of one to five carbon atoms, inclusive, monocyano substituted alkylthio of one to five carbon atoms, inclusive, phenylthio wherein phenyl is unsubstituted or substituted with one to three substituents, same or different, selected from the group consisting of halogen and lower-alkyl of one to four carbon atoms, inclusive, cyano, alkoxy having one to five carbon atoms, inclusive, phenyl, and hydrogen, with the proviso that when B is hydrogen, A is of the formula

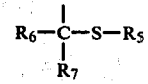

wherein R₅ is selected from the group consisting of alkyl of one to three carbon atoms, inclusive, and phenyl; R₆ is alkyl of one to three carbon atoms, inclusive; R₇ is selected from the group consisting of alkyl of one to three carbon atoms, inclusive, and SR₈, wherein R₈ is alkyl and is the same alkyl group as R₅, and taking R₅ and R₈ together with the atoms to which they are attached form a dithio heterocyclic of the formula

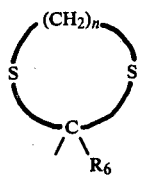

wherein n is 2 or 3 and the alkylene portion of the ring is unsubstituted or substituted with one or two methyl groups; A and B taken together with the carbon atom to which they are attached form a dithio heterocyclic of the formula

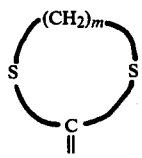

wherein m is 2 or 3 and the alkylene portion of the ring is unsubstituted or substituted with one to two methyl groups; and c.

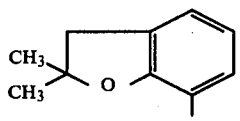

$R_1$ is selected from the group consisting of lower-alkyl, phenyl, substituted phenyl, phenlower-alkyl, and cycloalkyl; X is oxygen or sulfur; P is three or four; Ra is selected from the group consisting of hydrogen, lower alkyl, lower alkoxy, and halogen; and k is zero or one.

57. Formulation for pest control comprising an adjuvant carrier and a biologically effective amount of one or more N-[(phosphinyl)amino-thio- and N-[(phosphinothioyl)amino-thio-methylcarbamates as active ingredient represented by the schematic formulae:

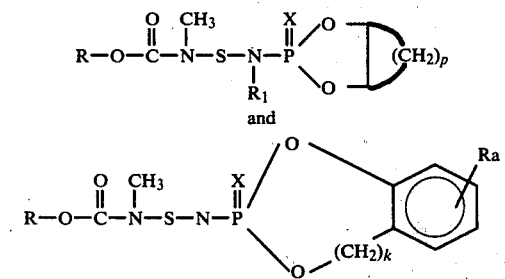

wherein R is selected from the group consisting of a.

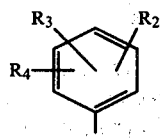

wherein $R_2$, $R_3$, and $R_4$ are the same or different and are selected from the group consisting of hydrogen, lower-alkyl of one to five carbon atoms, inclusive, halogen, lower-alkoxy of one to five carbon atoms, inclusive, lower-alkylthio of one to five carbon atoms, inclusive, dialkylamino with each alkyl the same or different and having one to three carbon atoms, inclusive, and N=CHN(CH₃)₂;

b.

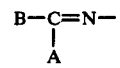

wherein A and B are the same or different and are selected from the group consisting of lower-alkyl of one to five carbon atoms, inclusive, loweralkylthio of one to five carbon atoms, inclusive, phenylthio wherein phenyl is unsubstituted or substituted with one to three substituents, same or different, selected from the group consisting of halogen and loweralkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when B is hydrogen, A is of the formula

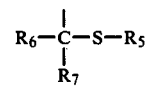

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula

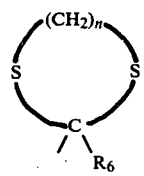

wherein n is 2 or 3 and the alkylene portion of the ring is unsubstituted or substituted with one or two methyl groups; A and B taken together with the carbon atom to which they are attached form a dithio heterocyclic of the formula

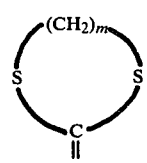

wherein m is 2 or 3 and the alkylene portion of the ring is unsubstituted or substituted with one to two methyl groups; and

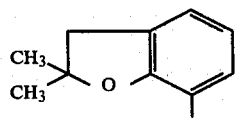

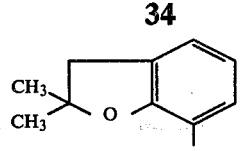

R₁ is selected from the group consisting of lower-alkyl, phenyl, substituted phenyl, phenlower-alkyl and cycloalkyl, X is oxygen or sulfur, P is three or four; Ra is selected from the group consisting of hydrogen, lower alkyl, lower alkoxy and halogen; and k is zero or one.

R₁ is selected from the group consisting of lower-alkyl, phenyl, substituted phenyl, phenlower-alkyl and cycloalkyl, X is oxygen or sulfur, P is three or four; Ra is selected from the group consisting of hydrogen, lower alkyl, lower alkoxy and halogen; and k is zero or one.

* * * * *